United States Patent [19]

Komatani et al.

[11] Patent Number: 5,179,580
[45] Date of Patent: Jan. 12, 1993

[54] X-RAY ANALYZER WITH SELF-CORRECTING FEATURE

[75] Inventors: Shintaro Komatani, Osaka; Shunji Nagao; Yoshihiro Wakiyama, both of Kyoto, all of Japan

[73] Assignee: Horiba Ltd., Kyoto, Japan

[21] Appl. No.: 843,623

[22] Filed: Feb. 28, 1992

[30] Foreign Application Priority Data

Mar. 2, 1991 [JP] Japan .................................. 3-61180

[51] Int. Cl.$^5$ ........................................ G01N 23/201
[52] U.S. Cl. ........................................ 378/44; 378/87; 378/88; 250/374
[58] Field of Search ................. 378/44, 45, 49, 48, 378/82, 86, 88, 90, 70; 250/261, 262, 374, 375, 387, 388

[56] References Cited

U.S. PATENT DOCUMENTS 4,090,074 5/1978 Watt et al. ........................ 378/88

Primary Examiner—Janice A. Howell
Assistant Examiner—Don Wong
Attorney, Agent, or Firm—Price, Gess & Ubell

[57] ABSTRACT

An X-ray analyzer capable of reducing the effects of a shift of peak positions in an energy spectrum resulting from a change in temperature and a lapse of time in an X-ray detector to enable a highly accurate analysis.

A shift of peak positions of X-rays from known positions are detected and a voltage applied to a proportional counter is controlled on the basis of the detected results. In addition, a gain in an amplifier amplifying an output from the X-ray detector may be controlled on the basis of the detected results.

12 Claims, 6 Drawing Sheets 5,179,580

X-RAY ANALYZER WITH SELF-CORRECTING FEATURE

BACKGROUND OF THE INVENTION

1. Field of the Invention

The present invention relates to an X-ray analyzer in which secondary X-rays, generated when primary X-rays from an X-ray source are incident upon a sample, are projected by an X-ray detector and elements contained in the sample can then be analyzed on the basis of an output from the X-ray detector, and more particularly, to a self-correcting feature to improve and maintain the accuracy of the output readings.

2. Description of Related Art

A conventional X-ray analyzer has a construction as shown in, for example, FIG. 6. In this FIG., reference No. 1 designates a sample, reference No. 2 designates an X-ray tube as one example of an X-ray source adapted to emit primary X-rays 3 towards the sample 1. A proportional counter 4 is one example of an X-ray detector capable of detecting the secondary X-ray 7, such as, for example, fluorescent X-rays 5 and scattered X-rays 6, that are emitted from the sample 1 when the primary X-rays 3 are incident upon the sample 1. These secondary X-rays are characteristic of the elements contained in the sample 1. The proportional counter 4 is operated by applying a predetermined high voltage from a high voltage source 8 and is capable of outputting an (eV) quantity of charges proportional to the energy of the detected X-rays.

An amplifier 9 can suitably amplify the output from the proportional counter 4, and this output can then be converted by an A–D converter to convert the analog signal put out from the amplifier 9 into a digital signal. A multi-channel analyzer 11 (hereinafter referred to as MCA) is capable of memorizing a predetermined number of output signals from the A–D converter 10 and to carry out a statistical analysis of these stored signals. A CPU 12 is capable of processing the signal output from the MCA 11 to determine the constituent elements in the sample.

In an X-ray analyzer of the conventional configuration, an energy spectrum is shown, for example, in FIG. 7 representing the output of the detector over an energy band of the detected X-rays, after the primary X-rays 3 were incident upon the sample 1. In FIG. 7, the mark (a) designates the detected count of fluorescent X-rays 5 of an element contained in the sample, while the mark (b) designates the detected count of the scattered X-rays 6. As can be seen, the X-rays designated by marks (a), (b) have energy levels characteristic of the individual elements of the sample and disclose a Gaussian distribution or a distribution corresponding to a substantially Gaussian distribution having peaks $(a_p)$, $(b_p)$, at specific positions across the energy spectrum. Based on this information, the element contained within the sample can be determined from the position of the peak $(a_p)$ and a concentration of the element contained within the sample can be measured from the total number of counts within an energy range $(a_1$ to $a_2)$ of the fluorescent X-rays 5. As can be appreciated, with such an X-ray analyzer, even though a sample may have a diverse number of elements contained therein, they can be sufficiently analyzed together along with their specific concentrations.

A problem can exist in such an X-ray analyzer having the above construction as a result of the effects of temperature and time on the performance of the electronic components that are utilized in the circuit, for example, if the proportional counter 4, the amplifier 9, or the A–D converter 10 changes in temperature, or even in some cases over a lapse of a period of time, then a signal gain that is determined through these elements can drift, and an error can be produced in the counting number of the fluorescent X-rays 5. If, for example, a signal gain is reduced, the energy spectrum, as shown by the full line in FIG. 8(a), is obtained. Alternatively, if the signal gain is increased, the energy spectrum, as shown by the full line in FIG. 8(b), would be obtained. As can be readily appreciated, in both examples, the energy spectrum has been greatly shifted from the desired energy spectrum, as shown by the dotted, imaginary lines in both figures and the corresponding position of the peaks $(a_p)$, $(b_p)$, also are shifted, resulting in an error in the analysis of the elements contained in the sample.

In order to avoid such a deterioration in the accuracy of measurement resulting from any shift in the peak positions $(a_p)$, $(b_p)$, that would occur, as mentioned above; attempts have been made to determine the peak position through an analysis of the output signals in a CPU 12. This method, however, requires a significant amount of data to be stored so that not only will a real time analysis be delayed, but also a problem has occurred in that the complexity of operation of the CPU 12 is significantly increased with both cost and the possibilities of error in the calculation being apt to occur.

The above described problems have also occurred in an X-ray analyzer using a Si (Li) detector and a Ge detector other than the proportional counter and also with an X-ray analyzer using a window comparator and a single-channel analyzer in place of the A–D converter 10 and the MCA 11, respectively. Thus, the prior art is still seeking to optimize, in an economical manner, the accuracy of an X-ray analyzer.

SUMMARY OF THE INVENTION

The present invention provides an X-ray analyzer capable of reducing any effects of a shift of peak position in an energy spectrum resulting from a change in temperature or a signal drift over a period of time, of not only the X-ray detector element itself, but also the electronic components used in processing the output of the X-ray detector to thereby maintaining a highly accurate analysis.

The advantages of the present invention are achieved in one solution to the above problems by controlling the voltage applied to a proportional counter after detecting any shift in the peak position of X-rays contained in the secondary X-rays. The peak positions of energy are ascertained and any shifting of these peak position of energy can, by appropriate signal processing, be detected with a corresponding adjustment in the applied voltage of the proportional counter to correct these errors. Another approach to resolving these problems is to adjust the gain in an amplifier that amplifies the output of the X-ray detector on the basis of the detected results, wherein again a shift of the peaks positions of the X-rays are determined to adjust the amplifier gain.

Although scattered X-rays, which are emitted from the sample, when the primary X-rays are incident from the sample have been used as the source of X-rays to be detected, is also possible to use for X-rays of a known element (Fe in this case) when it has been previously found, for example, that a base of the sample is Fe (iron). Thus, if a known element is utilized, having a predetermined peak position, shift positions from that known element can then be utilized to compensate for shift positions for unknown elements.

As can be readily appreciated, the implementation of determining the shift position from the output of the X-ray detector can be accomplished digitally with the assistance of software and a CPU, or could be accomplished with an analog circuit.

In implementing the first approach to the present invention, the shift in the peak positions of the secondary X-rays and the peak positions of energy from a known datum levels are detected and a voltage applied to the proportional counter is controlled on the basis of the detected results so that the voltage may be increased when a signal gain is reduced in the proportional counter and in any electronic components involved in processing the output of the proportional counter and, on the contrary, the voltage supply may be reduced when the signal gain in the proportional counter and the other electronic components is increased. Alternatively, any shift in the peak position of the secondary X-rays can also be detected and the gain in an amplifier that is used for amplifying the output of the X-ray detector could be controlled on the basis of the detected results so that a gain in the amplifier may be increased when a signal gain is reduced, resulting in a change in the characteristics of the X-ray detector and the other electronic components and the gain in the amplifier can be reduced when the signal gain is correspondingly increased.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an X-ray analyzer with a self-correcting feature.

Figure 6:
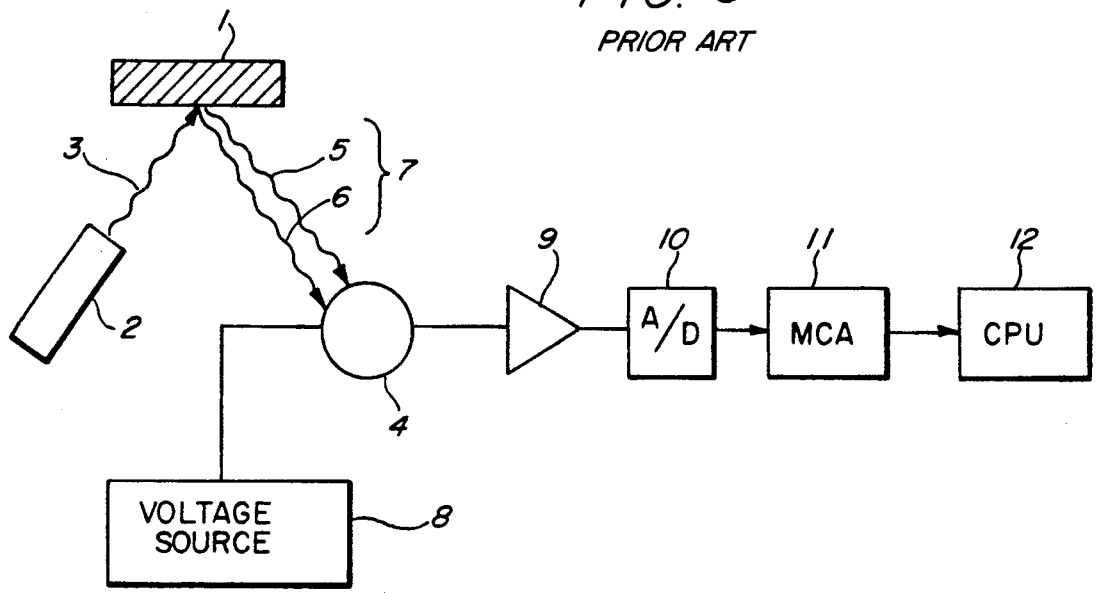
FIG. 6 is a block diagram showing the construction of a conventional X-ray analyzer.
Figure 7:
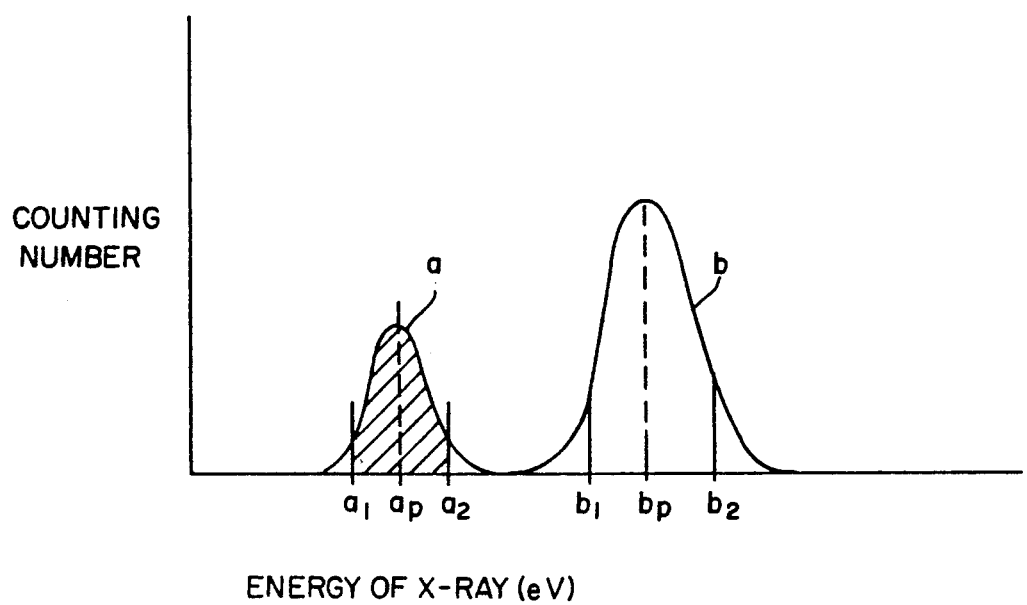
FIG. 7 is a diagram showing an energy spectrum of secondary X-rays emitted from a sample when primary X-rays are incident upon a sample.
Figure 8A:
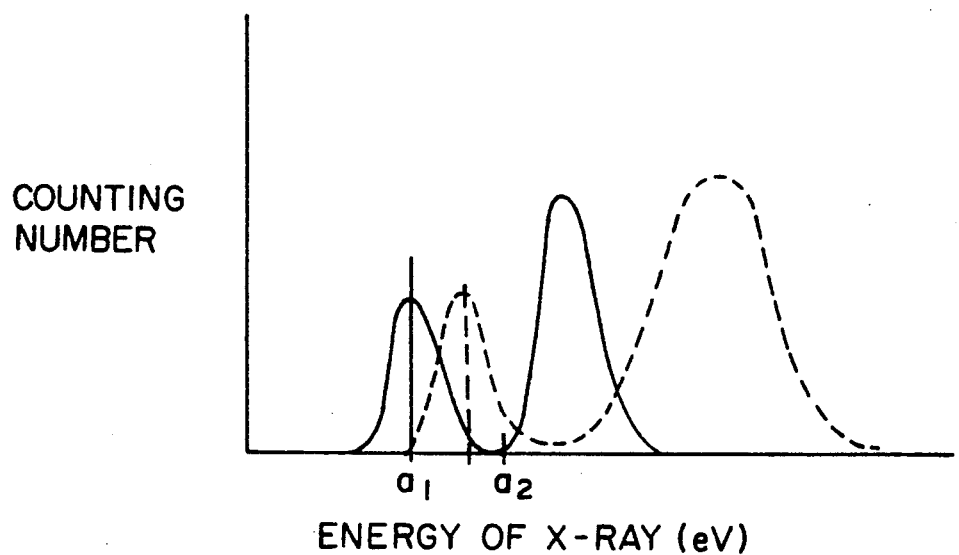
FIGS. 8(a) and 8(b) are diagrams disclosing the counting number of an X-ray detector versus the energy spectrum under various conditions of operation.
Figure 8B:
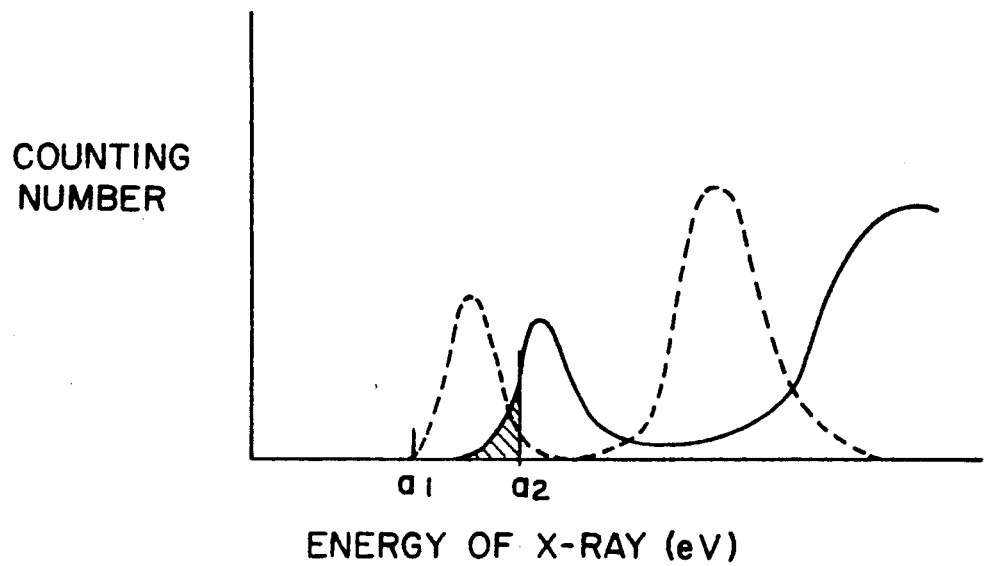

In the description of the preferred embodiment of the present invention, the same reference numbers that were utilized in the above descriptions of FIGS. 6 and 7 will be utilized again for the same component parts.

Figure 1:
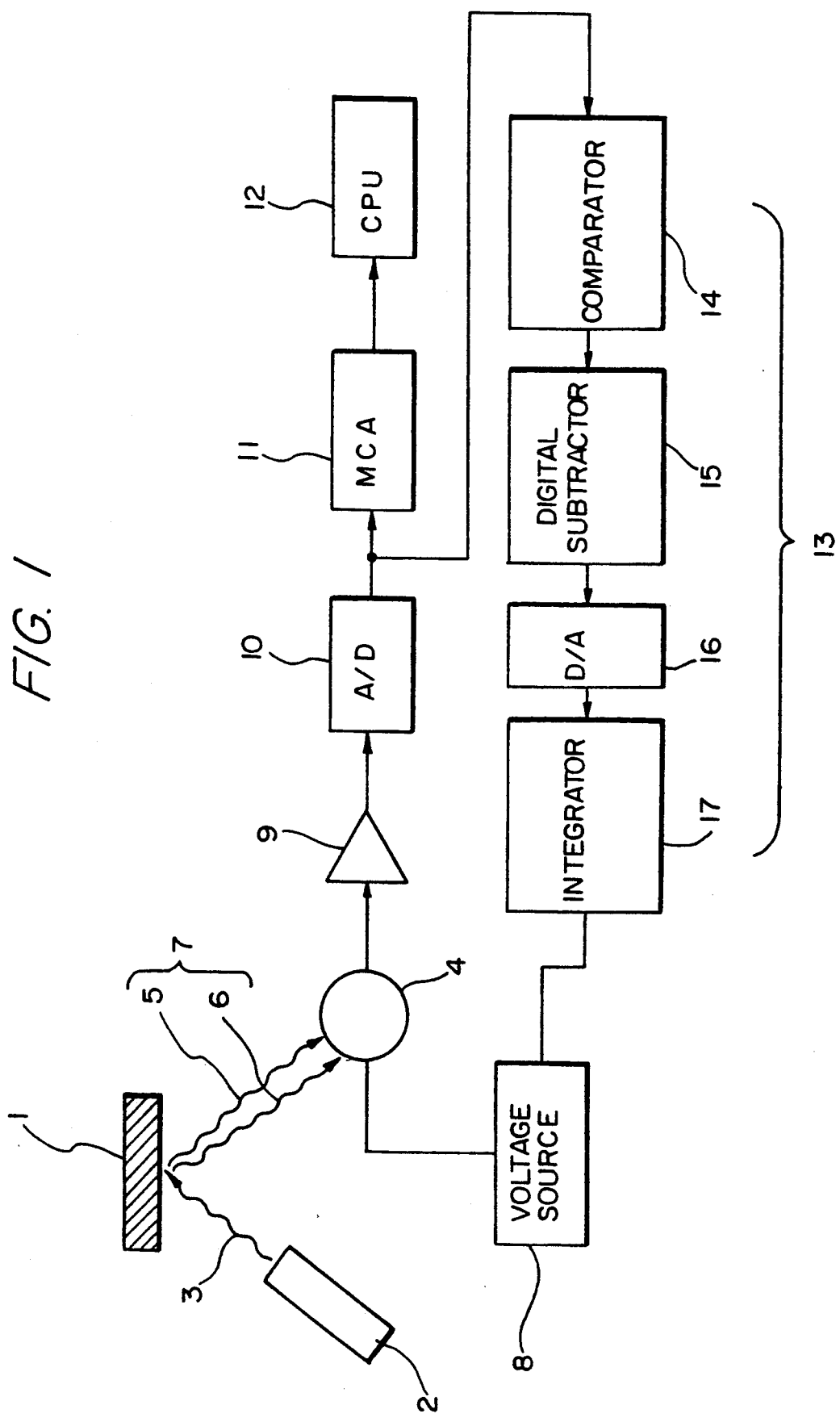
FIG. 1 is a schematic block diagram showing a construction of an X-ray analyzer according to a first embodiment of the present invention.

FIG. 1 discloses a first embodiment of the present invention wherein a signal processing circuitry 13 for feedback correction is utilized to determine any shift of peak positions during operation and includes a digital window comparator circuit 14, a digital subtractor circuit 15, a D–A converter circuit 16, and an integrator circuit 17 connected in series in that order so that an output from the A–D converter 10 may be sampled in the digital window comparator 14 and an output from the integrator 17 may be inputted to a control portion (not shown) of a high voltage power source 8 to vary the driving voltage to the proportional counter 4.

Figure 2A:
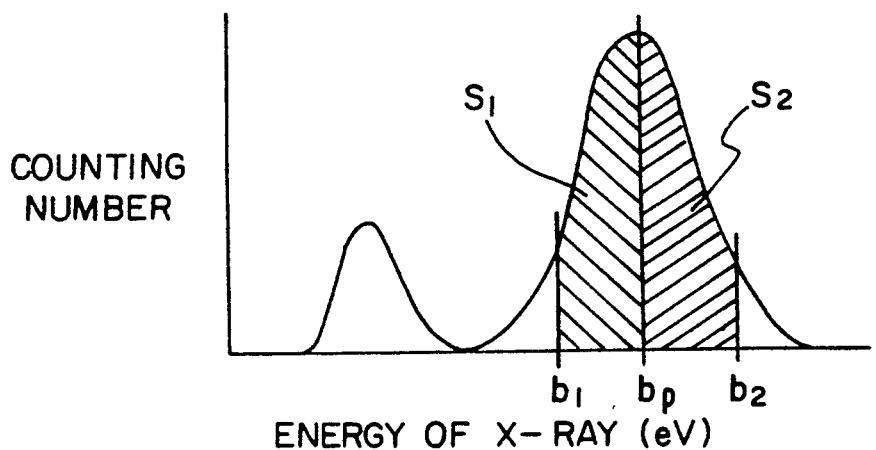
FIGS. 2(a), 2(b), and 2(c) are diagrams showing the operational output of the X-ray analyzer.
Figure 2B:
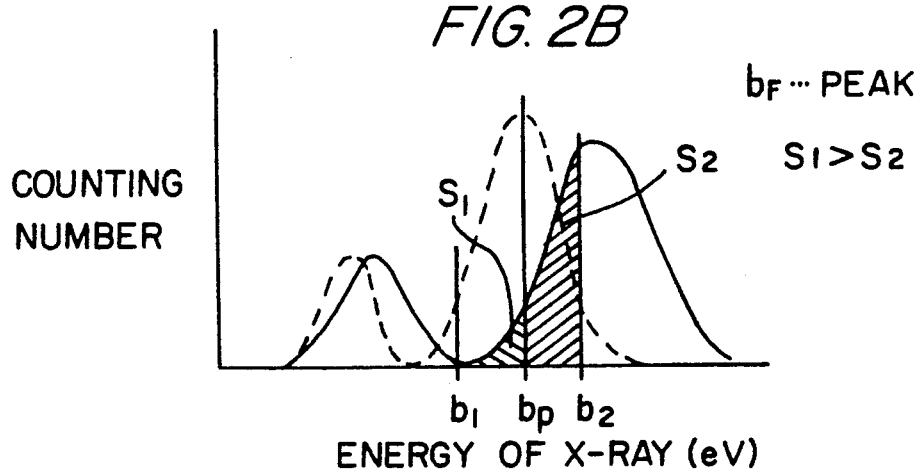
Figure 2C:
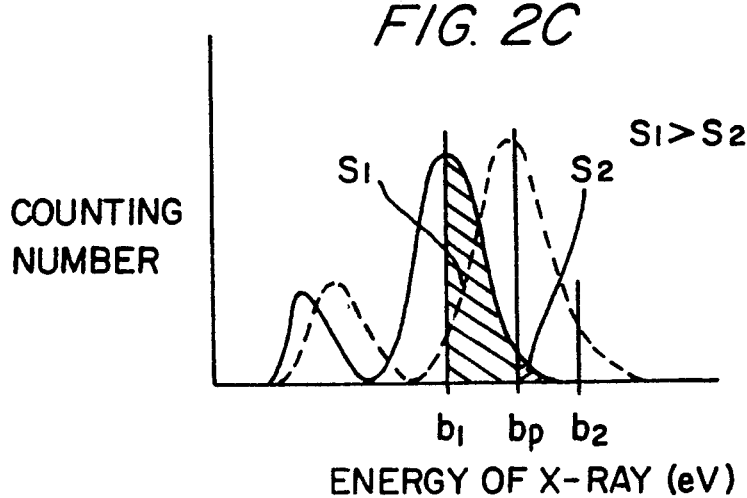

Any shift of the peak positions is detected in the feedback circuitry 13 as follows: In the digital window comparator circuit 14, it is discriminated whether an information ($\chi$) (eV) characteristic of the scattered X-ray 6, contained within the secondary X-ray 7, exists within an energy range $b_1$ to $b_2$, that is, whether an equality has been met, $b_1 < \chi < b_2$. In the case, where the above described condition is satisfied, then the digital subtractor 15 determines a difference between the information ($\chi$) and the peak energy ($b_p$), (wherein $b_p$ meets a relationship of $b_p - b_1 = b_2 - b_p$ in the scattered X-ray 6 is calculated to provide a subtracted output ($\chi - b_p$). Subsequently, this output ($\chi - b_p$) is converted into an analog signal in the D–A converter 16, followed by being integrated in integrator 17 so that a control signal is provided to the high voltage power source 8 to drive the proportional counter 4. An example of an applicable proportional counter are the Model D886 and Model D1286 proportional counters sold by Hamamatsu Photonics K.K. of 326—6, Sunayama-Cho, Mamamatsu-City, Japan. In the integrator 17, the information ($\chi$) of energy of the X-rays of several k counts/sec is obtained from the A–D converter 10 so that an analog quantity corresponds to an area (S2) minus an area S1), as shown in FIG. 2(a) is determined in the integrator 17. If S1 equals S2 holds good, the peak position exists at $b_p$ and if S1 less than S2 holds good, as shown in FIG. 2(b), the peak position exists on the side of $b_p$ in a signal gain is large. In addition, if S1 greater than S2 holds good, as shown in FIG. 2(c), the peak position exists on the side of $b_1$ and the signal gain is relatively small. Accordingly, although it is unnecessary to regulate the gain when the peak positions exists at $b_p$, a signal gain will be reduced when it is discriminated that the peak position exists on the side of $b_2$ while the signal gain is increased when it is determined that the peak position exists on the side of $b_1$.

Figure 3:
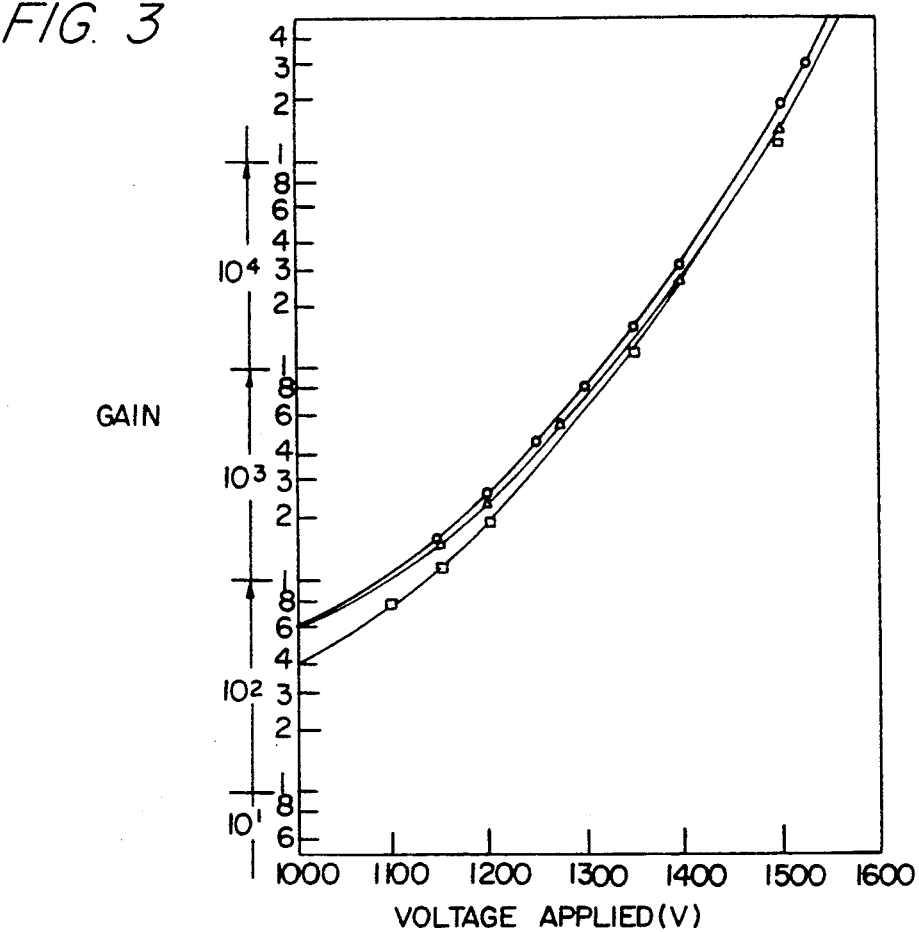
FIG. 3 is a chart showing the relationship between applied voltage to a proportional counter and its effect on gain.

Referring to FIG. 3, a relationship between gain and the voltage applied to the proportional counter is disclosed. By determining if a signal gain or signal decrease has resulted, it is possible to eliminate the problem of a shift in peak position by controlling the voltage applied to proportional counter 4 on the basis of the output from the integrator 17. That is, the voltage applied is increased when the signal gain is small, while the voltage applied is reduced when the signal gain is large.

Figure 4:
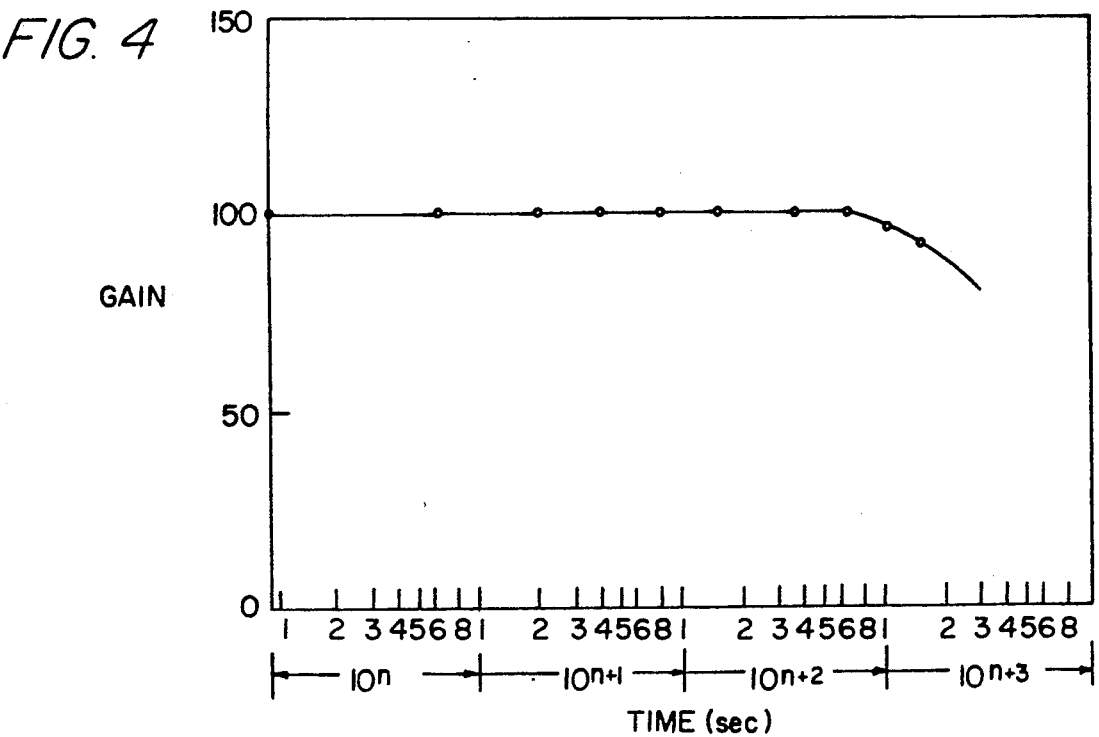
FIG. 4 is diagram showing the relationship between the stability of gain and the useful life time of a proportional counter.

An additional factor can impact the accuracy in that the proportional counter 4 has a relatively known useful life cycle which can be approximated in the diagram of FIG. 4. From this diagram, it can be seen that the normal useful life time of a proportional counter 4 will be within range of two to three years during most applications. This useful life time, however, can be increased by as much as a factor of ten, that is, to twenty or thirty years by controlling the voltage applied to the proportional counter 4 in the above described manner. As can be readily appreciated, a maintenance time cycle for inspecting or replacing a proportional counter 4 can also be accordingly carried out with an appropriate alarm, when a change of voltage applied to the proportional counter 4 exceeds a predetermined value.

Figure 5:
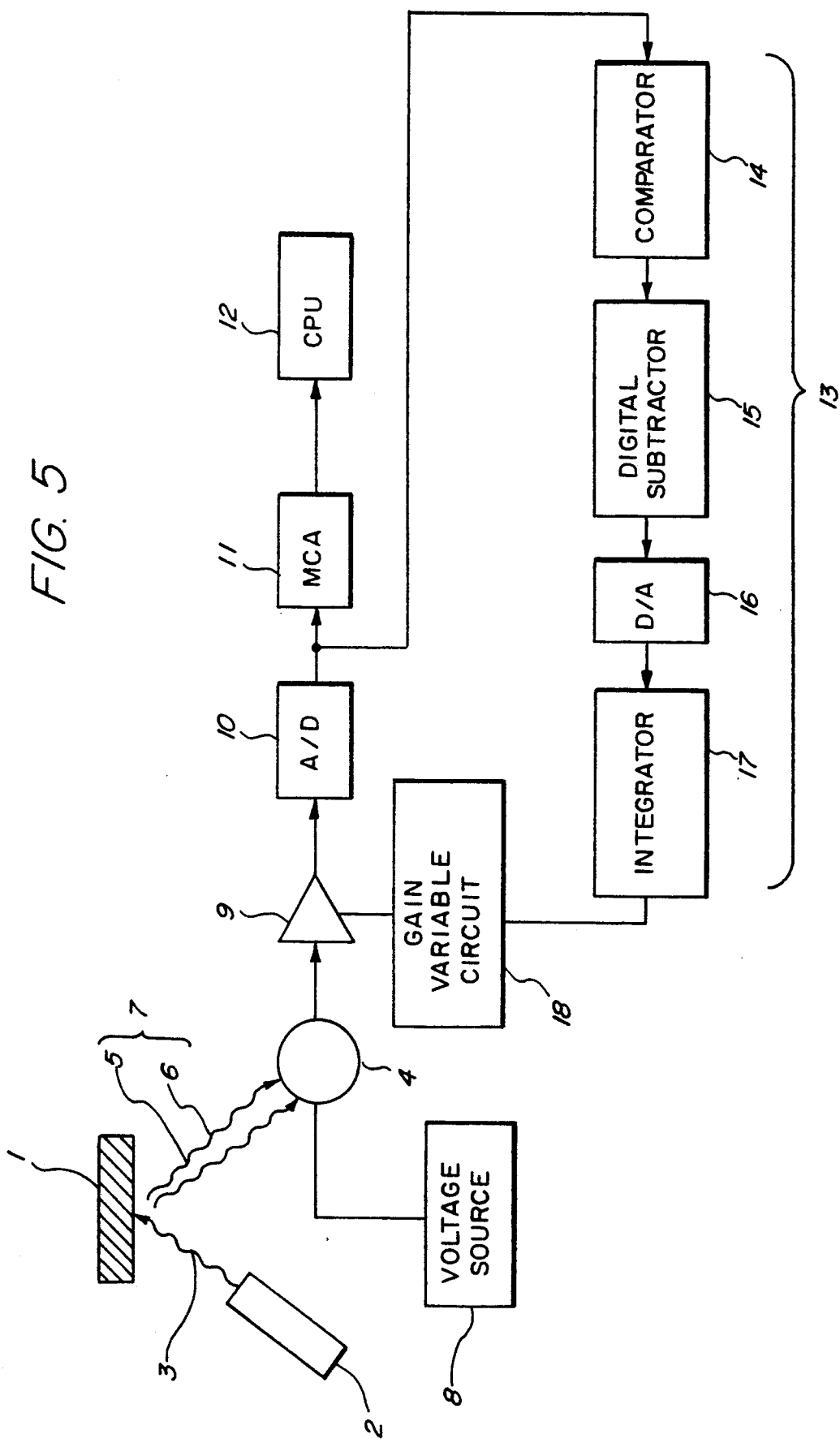
FIG. 5 is block diagram disclosing a construction of an X-ray analyzer in accordance with a second embodiment of the present invention.

FIG. 5 discloses an alternative embodiment of the present invention. In this embodiment, the gain in an amplifier 9 is controlled on the basis of the output from the integrator 17 from the feedback circuit 13. In FIG. 5, element 18 refers to a gain variable circuit and in this embodiment, control can be carried out so that the gain of the amplifier 9 may be increased when the signal gain is small and the gain in the amplifier 9 may be reduced when the signal gain is large. In implementing the present invention, the detector can, for example, be an Si (Li) detector, a GE detector and the like, to serve the function of the X-ray detector and proportional counter 4.

Although, in the preferred embodiment, the shift of the peak positions is digitally detected by means of a feedback circuitry 13 in each of the above described embodiments, the shift of peak positions can also be detected through a software signal processing by means of a CPU. In addition, the shift of the peak positions may be also be analogously detected in an analog fashion, and in this case, an analog window comparator can be used in place of the digital window comparator 14. The analog window comparator is connected so that an output in the amplifier 9 may be placed therein and an analog subtractor can be used in place of the digital subtractor 15 with the D-A converter 16 removed from the circuit. In addition, a window comparator circuit and a single-channel analyzer may also be used in place of the A-D converter 10 and the MCA 11, respectively.

In the above described embodiments, the scattered X-rays 6 were used as the detected X-rays within the secondary X-rays 7 with the peak positions being known and the shift of the peak positions in energy of the scattered X-rays is detected in the above described preferred embodiments. The reference position or peak position is determined depending upon the particular target of the X-ray tube in the X-ray analyzer. For example, in the case where titanium is used as the target, the reference position, that is, the position $b_p$ in FIG. 7, would exist at 4.56 KeV. It is possible, however, for the fluorescence X-rays of a known element to be used in the case where, for example, a basic element of the sample has been previously determined. This will provide a datum line for determining the relative shift in peak positions. For example, where it is known in advance that Iron (Fe) is contained in the sample to be measure (but the element to be measured is not iron), the fluorescent X-rays emitted from iron can be used and the reference position in this case exists at 6.4 KeV.

As above described, in both the first and second embodiments of the invention, a shift of peak positions in the energy spectrum, resulting, for example, by a drift of the signal gain, which occurs with temperature changes and over periods of time of operation of electronic components, can be significantly reduced and thus a highly accurate analysis by an X-ray analyzer can be achieved. In the first embodiment, when a proportional counter is used as the X-ray detector, its useful life time cycle can be remarkably increased and maintenance can be easily monitored. In the second embodiment of the invention, a further advantage occurs in that not only a proportional counter, but other forms of detectors can be used as the X-ray detector.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In an X-ray analyzer, in which secondary X-rays, generated when primary X-rays from an X-ray source are incident upon a sample, are detected by means of an X-ray detector and elements contained in the sample are analyzed on the basis of an output from the X-ray detector, the improvement comprising:
    a proportional counter means for measuring a shift in an energy spectrum of the detected X-rays, the response of the proportional counter means is a function of the amount of applied voltage to the X-ray detector, and
    means for varying the voltage applied to the proportional counter means in response to a shift in the energy spectrum.

2. An X-ray analyzer as in claim 1, wherein peak positions of the energy spectrum are measured, converted to a digital format and are detected by the varying means.

3. An X-ray analyzer as in claim 1, wherein the means for varying includes a computing circuit which detects the shift of peak to peak positions.

4. An X-ray analyzer comprising:
    a source of X-rays for providing a beam of X-rays to contact a sample;
    detector means for measuring secondary X-rays that result from impact of the X-ray beam on the sample, including
    an X-ray detector for measuring the secondary X-rays, the response of the X-ray detector is a function of the amount of applied voltage to the X-ray detector;
    means for determining the energy spectrum of the detected secondary X-rays including means for determining a shift in the energy spectrum, from a known energy spectrum position, and
    means for varying the amount of applied voltage to the X-ray detector in response to the determination of the shift in the energy spectrum to compensate for the shift.

5. An X-ray analyzer as in claim 4 wherein the X-ray detector is a proportional counter.

6. An X-ray analyzer as in claim 4 wherein the X-ray detector is a Si (Li) detector.

7. An X-ray analyzer as in claim 4 wherein the X-ray detector is a Ge detector.

8. An X-ray analyzer as in claim 4 further including means for determining when the applied voltage exceeds a predetermined level and producing a corresponding alarm signal.

9. An X-ray analyzer comprising:
a source of X-rays for providing a beam of X-rays to contact a sample;
detector means for measuring secondary X-rays that result from impact of the X-ray beam on the sample including an X-ray detector for measuring the secondary X-rays;
means for amplifying an output of the X-ray detector;
means for determining the energy spectrum of the detected secondary X-rays including means for detecting a shift in the energy spectrum from a known energy spectrum position, and
means for varying a gain of the amplifying means in response to the shift in the energy spectrum to compensate for the shift.

10. In an X-ray analyzer wherein secondary X-rays generated, when primary X-rays from an X-ray source are incident upon a sample, are detected by means of an X-ray detector and elements contained in said sample are analyzed on the basis of an output from said X-ray detector, the improvement comprising:
an amplifier for amplifying the output of the X-ray detector;
means for detecting any shift in peak positions of an X-ray energy spectrum, and
means for varying a gain of the amplifier in response to the means for detecting.

11. An X-ray analyzer as in claim 10 wherein the means for detecting any shift includes means for determining an energy position of a known element contained in either an X-ray source target or the sample.

12. An X-ray analyzer as in claim 11 wherein fluorescent X-rays emitted from iron define a reference position from which to determine any shift.

* * * * *